United States Patent [19]
Mahaffey et al.

[11] Patent Number: 5,948,012
[45] Date of Patent: *Sep. 7, 1999

[54] COLD THERAPY DEVICE

[75] Inventors: Mark V. Mahaffey; Jeffrey D. Lacheta, both of New Philadelphia, Ohio

[73] Assignee: Cincinnati Sub-Zero Products, Inc., Cincinnati, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/931,386

[22] Filed: Sep. 16, 1997

Related U.S. Application Data

[63] Continuation of application No. 08/647,128, May 9, 1996, abandoned.

[51] Int. Cl.[6] .................................................. A61F 7/00
[52] U.S. Cl. ................................... 607/104; 607/114
[58] Field of Search .......................... 606/27, 31; 607/96, 607/104–106, 108–112, 114; 165/46, 146; 126/204

[56] References Cited

U.S. PATENT DOCUMENTS

| | | | |
|---|---|---|---|
| 1,896,953 | 2/1933 | Hassell | 607/104 |
| 1,914,026 | 7/1933 | Kirk | 607/104 |
| 2,110,022 | 3/1938 | Kliesrath | 5/334 |
| 2,198,989 | 4/1940 | Cooley | 128/254 |
| 2,250,325 | 7/1941 | Barnes | 257/12 |
| 2,397,232 | 3/1946 | Barnes et al. | 257/12 |
| 2,726,658 | 12/1955 | Chessey | 128/400 |
| 2,753,435 | 7/1956 | Jepson | 219/39 |
| 2,802,088 | 8/1957 | MacCracken | 219/39 |
| 2,866,072 | 12/1958 | Smith | 219/39 |
| 2,885,189 | 5/1959 | MacCracken | 257/215 |
| 2,930,594 | 3/1960 | MacCracken | 257/306 |
| 3,869,871 | 3/1975 | Bybalko et al. | 607/104 |
| 3,894,213 | 7/1975 | Agarwala | 607/104 |
| 3,967,627 | 7/1976 | Brown | 128/400 |
| 3,988,577 | 10/1976 | Leitner et al. | 235/151.1 |
| 4,098,279 | 7/1978 | Golder | 128/400 |
| 4,101,874 | 7/1978 | Denison et al. | 340/606 |
| 4,108,146 | 8/1978 | Golder | 128/400 |
| 4,114,620 | 9/1978 | Moore et al. | 128/254 |
| 4,118,946 | 10/1978 | Tubin | 62/514 R |
| 4,149,541 | 4/1979 | Gammons et al. | 128/400 |
| 4,154,245 | 5/1979 | Daily | 128/400 |
| 4,167,663 | 9/1979 | Granzow et al. | 219/497 |
| 4,170,998 | 10/1979 | Sauder | 128/400 |
| 4,172,454 | 10/1979 | Warncke et al. | 607/104 |
| 4,179,745 | 12/1979 | Wuertele | 364/571 |
| 4,182,567 | 1/1980 | Laar et al. | 354/299 |
| 4,259,961 | 4/1981 | Hood, III | 607/104 |
| 4,267,611 | 5/1981 | Agulnick | 5/453 |
| 4,314,143 | 2/1982 | Bilstad | 219/497 |
| 4,338,944 | 7/1982 | Arkans | 128/400 |
| 4,343,987 | 8/1982 | Schimbke et al. | 219/287 |

(List continued on next page.)

*Primary Examiner*—Linda C. M. Dvorak
*Assistant Examiner*—Bryan K. Yarnell
*Attorney, Agent, or Firm*—Charles R. Wilson

[57] ABSTRACT

The cold therapy unit of this invention includes a small portable ice chest and an electronic control unit to provide a unit which is safe to use right after surgery and has a portion which may be taken home by the patient. The combined unit provides the safety and accuracy of an institutional unit and the practicality and affordability of a portable take home unit. The cold therapy device includes an electronic control unit similar to the current institutional units in that it includes a thermoelectric module along with its associated electronic controls and a pump. The electronic control unit includes couplings to connect hoses leading to the patient and the cooling pad. Further, the portable ice chest having a lid fitted with an electric fluid pump which includes quick connect couplings allowing the ice chest to be placed in fluid communication with the electronic control unit. Finally, the fluid pump is electrically connected to the electronic control unit.

6 Claims, 2 Drawing Sheets

U.S. PATENT DOCUMENTS

| | | | |
|---|---|---|---|
| 4,371,779 | 2/1983 | Maynard et al. | 219/328 |
| 4,459,468 | 7/1984 | Bailey | 219/490 |
| 4,467,178 | 8/1984 | Swindle | 219/330 |
| 4,613,746 | 9/1986 | MacLaughlin | 219/490 |
| 4,633,066 | 12/1986 | Chang et al. | 219/437 |
| 4,663,586 | 5/1987 | Swerlein et al. | 324/115 |
| 4,747,408 | 5/1988 | Chuan-Chih | 607/104 |
| 4,844,072 | 7/1989 | French et al. | 128/400 |
| 5,051,562 | 9/1991 | Bailey et al. | 219/506 |
| 5,128,517 | 7/1992 | Bailey et al. | 219/506 |
| 5,201,365 | 4/1993 | Siegel | 607/104 |
| 5,241,951 | 9/1993 | Mason et al. | 607/104 |
| 5,363,663 | 11/1994 | Chen | 607/104 |
| 5,441,533 | 8/1995 | Johnson et al. | 607/104 |
| 5,476,489 | 12/1995 | Koewler | 607/104 |

COLD THERAPY DEVICE

This application is a continuation of application Ser. No. 08/647,128 filed May 9, 1996, now abandoned.

FIELD OF THE INVENTION

This application relates to a cold therapy device used after surgery to reduce the swelling of the surgical site. More particularly, the invention describes a cold therapy device having a portable ice chest and pump for use in the patient's home which combines with an electronic control unit for use in institutional settings.

BACKGROUND OF THE INVENTION

Cold therapy devices have been used for a number of years to reduce the swelling in the body, especially after a surgery. It has been proven that the application of cold therapy to a surgical site immediately after surgery reduces the post surgical swelling about the site and can reduce recovery time. Cold therapy devices can range in technology from a simple ice pack to an electronically cooled unit having a plurality of precise controls and features. This application is concerned with units which pump a chilled fluid through a pad which is placed in close relationship to the surgical site. In general, such devices come in two basic forms. In one form a portable ice chest having a quantity of ice and water placed therein and an internal pump is used to pump cooled liquid through the patient pad. In a second form, a precisely controlled thermoelectric module is used to cool a quantity of liquid placed within a reservoir and pumped to the patient pad.

Currently, electronically controlled units are typically used in institutions due to their costs, and the portable ice chests are used as a take home device so that a patient can continue the cold therapy at home. Some institutions, in an effort to eliminate the capital costs associated with the larger units, have begun using the small portable units immediately after surgery and then send the unit home with the patient. The patient is charged for the take home unit. However, as described, the portable units use ice to chill water within the ice chest which requires frequent checking and recharging with a new quantity of ice. Therefore, the nurse or attendant must keep a watchful eye on the ice in the ice chest so that the patient will get the full benefit of cold therapy. The melt time of the ice is further enhanced by the heat generated by the small motor which generally extends into the ice chest to pump fluid from the chest to the pad. Further, the take home units are primarily designed for use in the home, after the patient has rehabilitated a few days in the hospital, and therefore have few controls. Immediately after surgery, the site may still be numb and the patient would be unable to determine if the fluid is too cold. While cold therapy is advantageous, it is possible to cool the tissue too much and thereby discourage healing or cause possible tissue damage. After the patient is home, he/she should have full feeling at this site and will be able to tell when the liquid is too cold. While the large institutional units employ precise temperature controls to prevent excessive cooling, the smaller take home units generally can only control the temperature of the liquid by restricting the flow of water through the pad.

The institutional units use large thermoelectric modules which use electricity to chill the liquid to its desired temperature. However, while these thermoelectric modules are well suited to maintain the temperature at the desired level, they require large amounts of energy to initially cool the liquid. Further, while the thermoelectric modules are cooling the liquid, they generate significant heat which must be blown out of the unit by electric fans to prevent the electronics from overheating and to prevent the simultaneous heating and cooling of the liquid.

SUMMARY OF THE INVENTION

The cold therapy device of this invention addresses the limitations of the institutional unit and the small take home unit by combining the two units into a hybrid cold therapy unit. The cold therapy unit of this invention includes a small portable ice chest and an electronic control unit to provide a unit which is safe to use right after surgery and has a portion which may be taken home by the patient. The combined unit provides the safety and accuracy of an institutional unit and the practicality and affordability of a portable take home unit. The cold therapy device includes an electronic control unit similar to the current institutional units in that it includes a thermoelectric module along with its associated electronic controls and a pump. The electronic control unit includes couplings to connect hoses leading to the patient and the cooling pad. Further, the portable ice chest having a lid fitted with an electrical fluid pump which includes quick connect couplings allowing the ice chest to be placed in fluid communication with the electronic control unit. Finally, the electrical fluid pump is electrically connected to the electronic control unit.

In operation, the ice chest is placed on top of the electronic control unit and filled with a quantity of ice and water and the lid of the ice chest is placed in position. The electronic unit is connected to tubing leading to and from the patient pad. When the unit is turned on and a temperature is set on the control panel of the electronic unit, the electronic control unit turns on the fluid pump and its own internal pump to fill the fluid path from the electronic unit to the patient pad with water. When the fluid path is filled, the control unit turns the fluid pump off. The electronic control unit monitors the temperature in the fluid path. The electronic control unit continues to pump the chilled fluid through the fluid path and makes minor adjustments to the temperature to keep it within a predetermined range by turning the thermoelectric module on and off. Since the thermoelectric module is only used to maintain the temperature and not initially cool the liquid, it is possible to use a smaller module requiring less energy and giving off less heat. If the temperature of the fluid rises beyond the predetermined range, the controller activates the ice chest fluid pump and places the ice chest in the fluid path to circulate the ice cold fluid in the ice chest through the fluid path unit until the temperature is again within range. It is, therefore, evident that the fluid pump is only on for short periods of time and therefore will not generate significant heat. Therefore, the ice in the portable ice chest will last for an extended period of time as compared to a system wherein the fluid pump is on for the entire time.

When the patient is discharged, the portable ice chest is disconnected from the control unit and is sent home along with a tubing set and a patient pad so that the patient can continue cold therapy. In its take home mode, the portable unit is filled with ice and water to supply cold therapy to the patient. As with other take home units, the temperature of the patient pad is controlled by a manual flow valve adjacent the pump. Restricting the fluid flow through the pad increases the temperature at the pad; conversely, increasing the fluid flow to the pad decreases the temperature at the pad.

The cold therapy device of this invention therefore provides the benefit of precise electronic control for use in the hospital and provides a cost effective take home unit for the patient. Further, by using the ice chest fluid pump sparingly, it is anticipated that a nurse or technician will need to fill the ice chest only once during the normal post operative hospital stay.

Accordingly, it is an object of this invention to provide for a novel cold therapy device.

Another object of the invention is to provide for a cold therapy device which combines the benefits of an electronic institutional cold therapy device with a portable take home device.

Another object of the invention is to provide for a novel cold therapy device wherein having an ice chest for storing a quantity of chilled liquid and ice connectable in flow communication to an electronic cold therapy device having a thermal module and pump.

Other objects of the invention will become apparent upon a reading of the following descriptions taken with the accompanying drawings.

DESCRIPTION OF THE PREFERRED EMBODIMENT

The preferred embodiment herein described is not intended to be exhaustive or to limit the invention to the precise form disclosed. Rather it is chosen and described to describe the invention so as to enable others skilled in the art to utilize its teachings.

Figure 1:
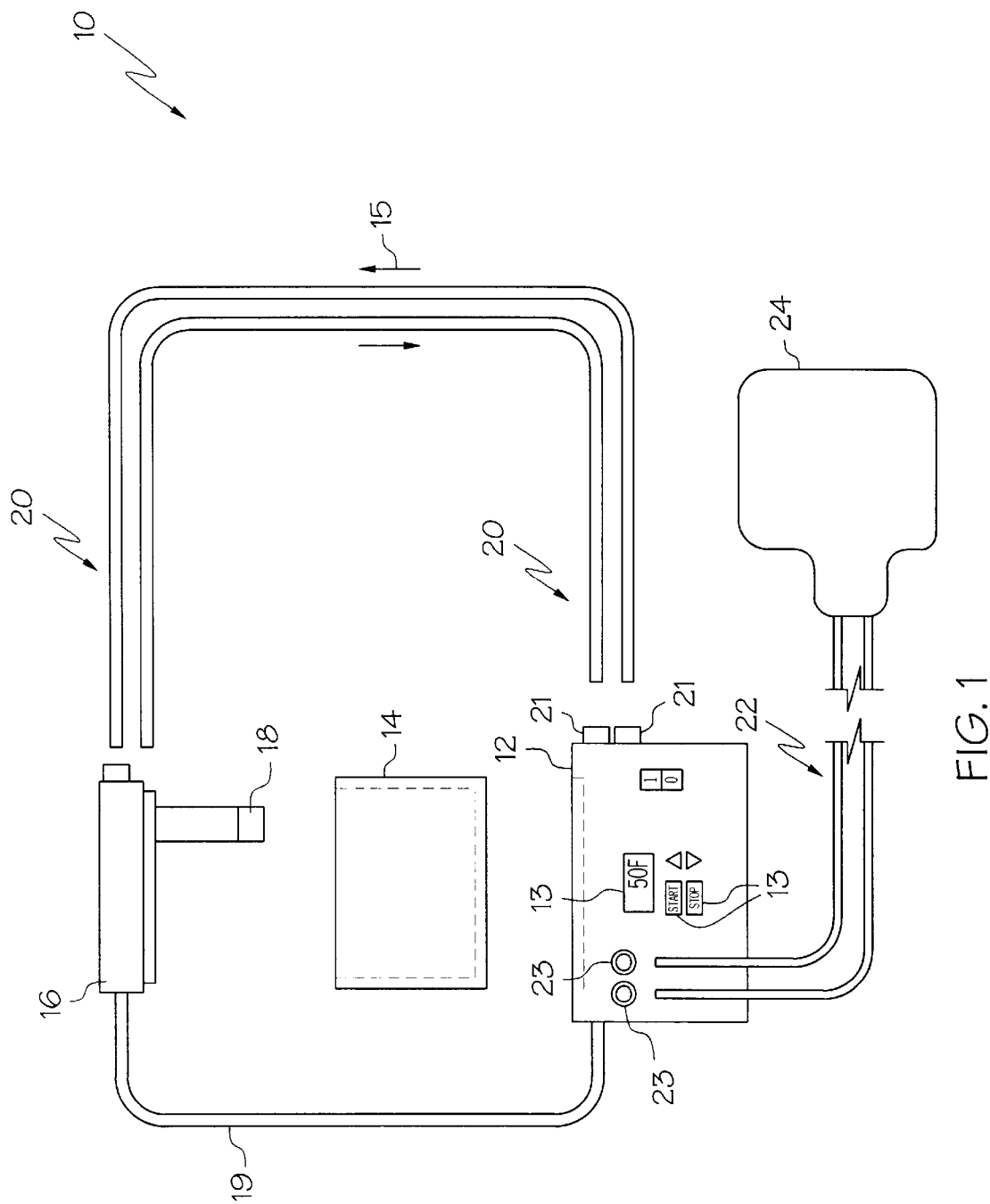
FIG. 1 is an diagrammatic view of the cold therapy unit of the invention with the components spaced from one another for illustrative purposes.

Referring now to the figures, cold therapy unit 10 includes an electronic control unit 12 having a housing which accommodates a reservoir, e.g. an ice chest 14. Ice chest 14 includes a lid 16 having a manual flow control valve 17 and a first fluid pump 18. A set of hoses 20 connect first fluid pump 18 to input ports on the electronic unit 12, preferably via quick connect hose couplings as are commonly understood in the industry. An electronic power supply line 19 from first fluid pump 18 is electrically connected to a D.C. power supply in the electronic unit. As illustrated in FIG. 1, first fluid pump 18 is configured to extend into the ice chest 14.

A set of hoses 22 connect a cold therapy pad 24 to the output of the electronic control unit 12. Again, it is preferable if the hoses 22, electronic control unit 12 and therapy pad 24 are connected using quick connect hose couplings as are well known in the industry.

Figure 2:
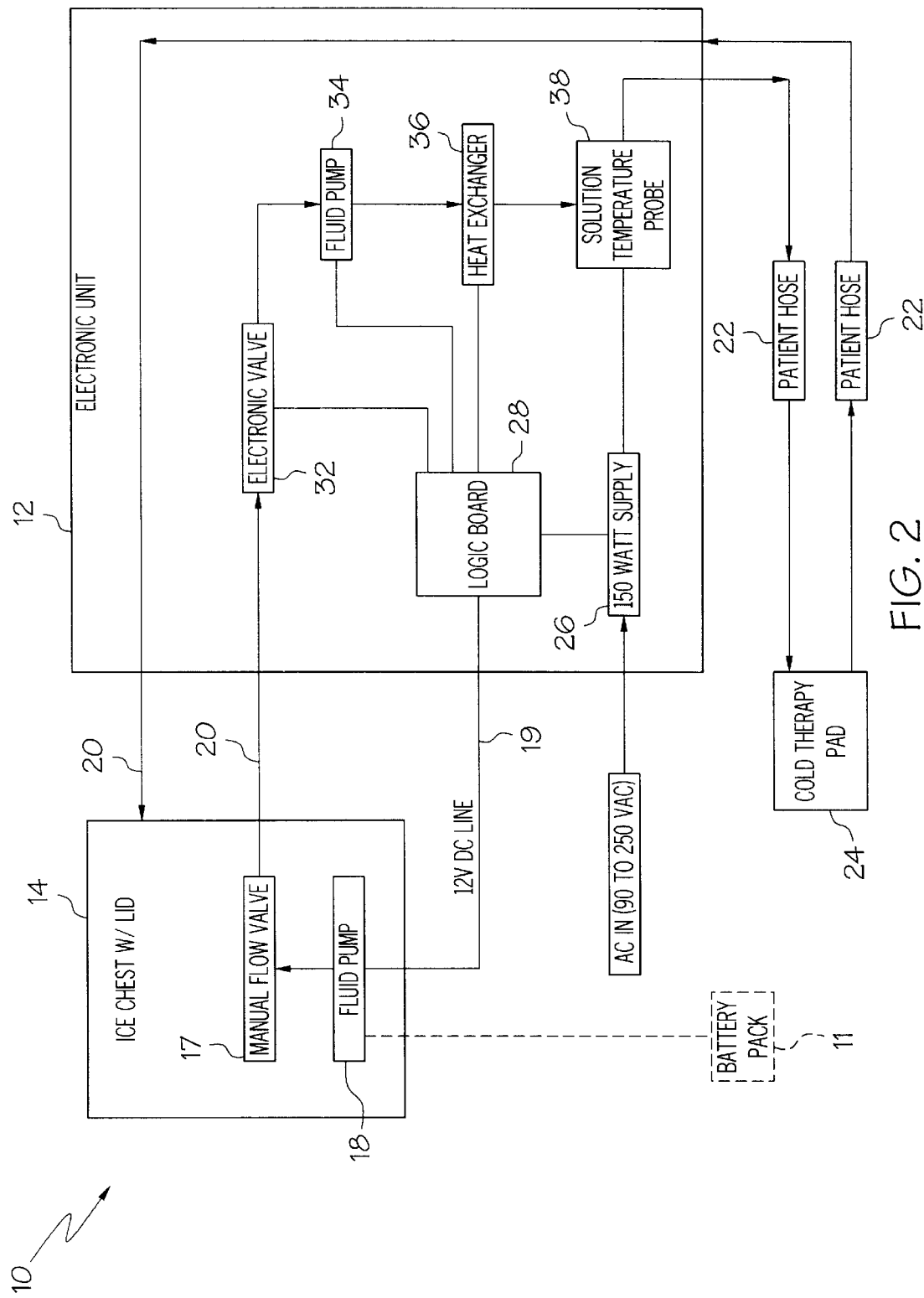
FIG. 2 is a block diagram of the invention.

Referring to FIG. 2, electronic control unit 12 includes a logic means, e.g. logic board 28 having a power supply 26, an electronic valve 32, a second fluid pump 34, a heat exchanger, i.e. a thermoelectric module 36 and temperature probe 38 electrically connected thereto. The electronic valve 32, fluid pumps 18 and 34, thermoelectric module 36 all being responsive to electronic signals sent from the controller. Power supply 26, as is well known, converts the AC line voltage to a usable and safe voltage for the surrounding components. The components of the electronic unit and ice chest, which make up the cold therapy unit 10 of the invention, as illustrated in block diagram form for simplicity, are believed to fully describe the invention to one fully skilled in the art. It should be understood that the lines between the blocks that terminate in an arrow head indicate a fluid path, wherein the lines between the blocks without such arrow heads are used to indicate a logical or electronic connection between the blocks. As illustrated in FIG. 1, electronic control unit 12 may include a plurality of input/output devices 13 on its front panel to provide for the starting and stopping of the unit and establishing a desired fluid temperature. Other such controls may be added as are well known and have no bearing on the subject invention, they will not be discussed further.

In use, in a hospital setting, the ice chest 14 is carried by the electronic control unit 12 or otherwise closely associated therewith. The electric power supply line 19 from first fluid pump 18 is connected to the electronic unit. Hoses 20 are connected between first fluid pump 18 and input receptacles 21 of the electronic control unit 12. Again, it is preferable that all connections between the various hoses and the electronic unit and first fluid pump 18 be accomplished by quick connect couplings (not shown) as are well known in the industry. A therapy pad 24 is connected to hoses 22 which are subsequently connected to the output receptacles 23 on electronic control unit 12. It should be understood that while the terms "input" and "output" have been used to describe the hose connections, the fluid is pumped from electronic control unit 12 in a circular path exiting one of the output connectors passing through one hose 22 and the pad to return via the other hose 22 and enter the electronic control unit 12 via the other "output" receptacle. Similarly, and with reference to FIG. 1, when the ice chest is placed in the flow path, liquid travels through one hose 20 in the direction of the arrow and returns through the other hose in the direction of the arrow 15.

After the ice chest and electronic unit have been connected as described above, a quantity of ice and water (preferably two liters of water and five pounds of ice) are placed into the ice chest, and lid 16 is secured into position and the unit is turned on to supply electricity to the logic board and electronic control unit. The operator using the input devices 13 on the control panel selects the desired temperature and turns on the second fluid pump 34 using the input device on the control panel. Initially, logic board 28, senses the lack of fluid in the flow path by receiving a signal from the fluid sensor (not shown) and activates first fluid pump 18. First fluid pump 18, when activated, pumps fluid from the ice chest through the flow path until the flow sensor (not shown) detects fluid flow and the logic board deactivates first fluid pump 18. As first fluid pump 18 is turned on, the logic board opens electronic valve 32 to place the first fluid pump 18 and ice chest in the flow path. When the pump is deactivated by the logic board, the electronic valve 32 is closed to take hoses 20, the ice chest 14 and first fluid pump 18 out of the flow path. During the cold therapy session, the temperature of the fluid in the fluid path is monitored by the solution temperature probe 38 which sends a signal to the logic board 28. When the logic board detects a rise in temperature above the set point as established by the operator, the logic board activates the thermoelectric module 36 to chill the fluid in the fluid path to the appropriate temperature. During the cold therapy session, it is possible for the temperature of the solution to exceed the set point temperature by an amount beyond the capabilities of the thermoelectric module to correct in an efficient manner. In such instances, the logic board opens electronic valve 32 and turns on first fluid pump 18 to reinfuse the fluid in the flow path with the ice cold liquid within the ice chest. When the temperature has decreased to a temperature at or near the set point, the logic board again shuts off first fluid pump 18 and closes the electronic valve 32 and relies on maintenance of the temperature by the thermoelectric module 36. Finally, if the temperature within the fluid path is lower than the set point, the logic board can activates the thermoelectric module 36 to heat the fluid until it reaches the set point. In this manner, the operator cam be assured that cold therapy will occur at the temperature selected by the operator.

As can be seen, in the institutional mode of operation for the cold therapy unit 10 of the invention, first fluid pump 18 is on for a relatively short period of time. Therefore, since the first fluid pump 18, which is in contact with the ice in ice chest 14, is not turned on for extensive periods of time, it does not generate excessive heat which would encourage melting of the ice. It is anticipated that using the therapy device of the invention, the ice within the ice chest will last for the entire post operative hospital stay. Therefore, the amount of nurse or attendant input is significantly decreased while using the therapy unit of the invention as compared with a standard portable ice chest therapy device. Further, during the hospital stay, the electronic control unit monitors the temperature of the fluid to ensure that the patient pad does not get too cold and thereby discourage healing or damage tissue.

When the patient is released from the hospital, the operator disconnects the hoses 20 from lid 16 and disconnects the hoses 22 and electric power supply line 19 from electronic control unit 12. The operator then connects hoses 22 to lid 16 of the ice chest 14. The ice chest is then removed from the electronic control unit 12 and sent home with the patient. An adapter may be sent along the ice chest to convert the typical 110 volt AC house voltage to a usable D.C. voltage for the pump. Alternatively, the lid could include the appropriate circuitry to allow the unit to be plugged directly into the patient's house voltage. During cold therapy at home, the patient fills the ice chest with water and ice, connects the hoses 22 and therapy pad 24 and then turns the unit on. First fluid pump 18 will pump chilled liquid through the hoses and pads and ice chest continuously until turned off. As illustrated, a manual flow control valve 17 is connected in flow communication with first fluid pump 18 and can be adjusted by the user to adjust the flow rate of the fluid through the pad. As the flow rate is decreased, the temperature of the pad increases since the fluid is being returned to the ice chest at a slower rate. Since the pump is continuously active, the heat it generates will reduce the useful life of the ice and water in the ice chest. Nevertheless, the ice will last for several hours which is sufficient during the continued recovery of a patient at home.

After the patient is fully recovered an auxiliary lid (not shown) may be provided which fits the ice chest to enable the patient to use the ice chest as a cooler for food or beverages. Since the first fluid pump 18 and manual flow control valve 17 are contained within the lid 16, and the ice chest is structurally intact without modification, the ice chest is usable in the more practical aspects of food or beverage storage by the patient.

Finally, referring to FIG. 2, a battery pack 11 is illustrated in block form and broken lines to indicate that a battery pack may be supplied with the unit to run first fluid pump 18 and supply chilled fluid to the patient during transport of the patient home.

It should be understood that while the invention has been described using a 12 volt D.C. pump, such should not be considered a limitation on the invention. Any small electric pump could be utilized in keeping with the teachings of the invention.

Further, it should be understood that the invention is not to be limited to the precise forms disclosed, but rather, may be modified within the keeping of the appended claims.

We claim:

1. A device for circulating a temperature controlled liquid through a therapy pad, the device comprising;
    a reservoir configured for holding a quantity of liquid,
    a first pump extending into said reservoir,
    a first hose set connected to said reservoir,
    a second hose set connected to the therapy pad, and
    an electronic control unit, said control unit being placed in flow communication with said reservoir and the pad by said first and second hose sets, further said control unit having a logic means, a second pump for pumping liquid through said hose sets and the pad, a thermoelectric module for adjusting temperature of the liquid within a predetermined range, and a temperature probe for generating a signal representative of the temperature of the liquid pumping through said hose sets and pad,
    said logic means controlling operation of said second pump and said thermoelectric module and comparing the signal from said temperature probe to a predetermined set point, said control unit further including a valve in flow communication with said reservoir and said hose sets such that with said valve open, said reservoir, hose sets and pad are in flow communication and the liquid is pumped through said reservoir, hose sets and pad, and with said valve closed said reservoir is isolated from said hose sets and the pad and the liquid is pumped through said hose sets and pad and still further said logic means controlling operation of said first pump wherein when the temperature of the fluid being pumped by said second pump exceeds a predetermined temperature, said logic means causes said valve to open to place said reservoir in flow communication with said hose sets and the pad and said first pump, further when the temperature of the fluid being pumped by the said second pump exceeds the predetermined temperature said first pump is turned on to pump fluid from said reservoir into said hose sets and pad.

2. The device of claim 1 wherein said reservoir, said first pump, said hose sets and the pad are removable from said electronic control unit, said first pump being configured to be operable independently of the electronic control unit when removed therefrom to pump liquid from said reservoir through said first hose set and pad.

3. A small portable cold therapy unit having a reservoir for holding a quantity of liquid, a first pump extending into the reservoir for pumping fluid from the reservoir, a hose set and pad connectable to the pump for receiving fluid pumped from the first pump and returning it to the reservoir after the fluid has traveled through the pad, the cold therapy unit removably connected to an electronic control unit having a second pump such that the electronic control unit is in flow communication with the pad and hose set and monitors the temperature of the liquid relative to a predetermined set point, wherein if the electronic control unit senses that temperature of the liquid exceeds the predetermined set point the control unit turns on the first pump in the portable cold therapy unit to reinfuse the liquid within the pad and hose set with a quantity of chilled liquid.

4. The unit of claim 3 wherein the electronic control unit includes a valve means responsive to the control unit which is operable by the control unit to place the first pump and reservoir in flow communication with the hose set and pad when electronic control unit senses the temperature of the fluid in the hose set and pad exceeding a predetermined temperature.

5. A cold therapy unit for circulating a temperature controlled liquid to a patient therapy pad, said cold therapy unit comprising:

(a) a reservoir configured for holding a quantity of liquid;

(b) a first fluid pump in flow communication with liquid in said reservoir;

(c) an electronic control unit, said electronic control unit in flow communication with said reservoir; and (d) a patient therapy pad in flow communication with said reservoir and said electronic control unit, further the electronic control unit having a logic means, a second fluid pump for pumping liquid to said therapy pad, a thermoelectric module for adjusting temperature of the liquid within a predetermined range, a temperature probe for generating a signal representative of the temperature of the liquid pumping to said therapy pad, and an electronic valve in flow communication with said reservoir, said logic means controlling the operation of said second pump and said thermoelectric module and comparing a signal from said temperature probe to a predetermined set point, said control unit further controlling operation of said electronic valve such that with said electronic valve open, said reservoir and therapy pad are in flow communication and the liquid is pumped through said reservoir and therapy pad, and with said electronic valve closed said reservoir is isolated from said therapy pad and the liquid is pumped through said therapy pad.

6. The cold therapy unit of claim 5 wherein the first fluid pump extends into said reservoir.

* * * * *